(12) United States Patent
Strait et al.

(10) Patent No.: US 11,590,090 B2
(45) Date of Patent: Feb. 28, 2023

(54) ACETAMINOPHEN FORMULATION WITH PROTECTION AGAINST TOXIC EFFECTS OF OVERDOSE

(71) Applicant: Anzen Pharmaceuticals, LLC, Ashland, VA (US)

(72) Inventors: Kevin M. Strait, Ashland, VA (US); Daniel J. Strait, Prescott Valley, AZ (US); Cameron D. Kawato, Chesapeake, VA (US)

(*) Notice: Subject to any disclaimer, the term of this patent is extended or adjusted under 35 U.S.C. 154(b) by 243 days.

(21) Appl. No.: 17/019,494

(22) Filed: Sep. 14, 2020

(65) Prior Publication Data

US 2021/0077433 A1 Mar. 18, 2021

Related U.S. Application Data

(60) Provisional application No. 62/900,479, filed on Sep. 14, 2019.

(51) Int. Cl.
| | |
|---|---|
| *A61K 9/24* | (2006.01) |
| *A61K 31/167* | (2006.01) |
| *A61K 31/198* | (2006.01) |
| *A61K 9/28* | (2006.01) |

(52) U.S. Cl.
CPC ............ *A61K 31/167* (2013.01); *A61K 9/209* (2013.01); *A61K 9/28* (2013.01); *A61K 31/198* (2013.01)

(58) Field of Classification Search
None
See application file for complete search history.

(56) References Cited

U.S. PATENT DOCUMENTS

| | | | |
|---|---|---|---|
| 6,566,401 B2 | 5/2003 | Herzenberg | |
| 9,415,016 B2 | 8/2016 | Friedl | |
| 2008/0139654 A1 | 6/2008 | Soderling | |
| 2016/0067189 A1* | 3/2016 | Becker | A61K 31/198 514/562 |

FOREIGN PATENT DOCUMENTS

WO WO-2009118764 A1 * 10/2009 ........... A61K 31/167

* cited by examiner

*Primary Examiner* — Susan T Tran
(74) *Attorney, Agent, or Firm* — Ryuh Patent Law; Steven Yu

(57) ABSTRACT

An oral pharmaceutical dosage form that comprises both acetaminophen and a glutathione replenishing agent, such as N-acetylcysteine. This allows co-administering the glutathione replenishing agent along with acetaminophen, which may be beneficial in rapidly counteracting the toxic effects of acetaminophen overdose. The oral dosage form could be in the form of a tablet or capsule. The dosage form may be designed to compartmentally separate the glutathione replenishing agent from having chemical interaction with the acetaminophen. The dosage form may be designed to mask the taste or smell of the glutathione replenishing agent.

12 Claims, 3 Drawing Sheets

ACETAMINOPHEN FORMULATION WITH PROTECTION AGAINST TOXIC EFFECTS OF OVERDOSE

TECHNICAL FIELD

This invention relates to solid pharmaceutical dosage formulations of acetaminophen.

BACKGROUND

Acetaminophen (or paracetamol) is one of the most widely used analgesic and antipyretic drugs. Acetaminophen is also present in many combination drug products. Of particular note are the opioid/acetaminophen combination products, such as the combination hydrocodone and acetaminophen in Vicodin®. Although considered to be highly safe, one of the major problems with acetaminophen is its liver toxicity (hepatoxicity). Acetaminophen overdose is responsible for about 50% of the cases of acute liver failure in the United States. In parallel with the epidemic of opioid abuse and the popularity of acetaminophen/opioid combination products, the incidence of acetaminophen overdose has been on the rise.

Upon ingestion, acetaminophen is metabolized in the liver, where most of the drug is conjugated with glucuronide and sulphate so that it can be eliminated via bile or urine excretion. A small fraction, about 5%, is metabolized in the liver by the cytochrome P450 mixed-function oxygenase system, which converts the drug to N-acetyl-p-benzoquinone imine (NAPQI). This NAPQI metabolite is toxic to the hepatocytes in the liver, where it damages proteins by covalently binding to nucleophilic cysteine residues. NAPQI is detoxified by conjugation with glutathione, a sulfhydryl donor, so that it can be excreted into bile or further metabolized into less harmful products. However, in acetaminophen overdose, the supply of glutathione is rapidly depleted. Without the ability to detoxify NAPQI, the hepatocytes die and the liver undergoes necrosis.

Acetaminophen overdose is treated by administering sulfhydryl compounds as an antidote, in particular, N-acetylcysteine (NAC). There are other less commonly used sulfhydryl compounds, such as glutathione, methionine, cysteine, and cysteamine. NAC counteracts the toxic effect of NAPQI by replenishing the supply of glutathione. Early administration of the antidote after overdose is critical. The optimal time for administration of NAC as a protective antidote is within 8 hours after the overdose. Thus, NAC should be given as soon as possible after acetaminophen overdose.

SUMMARY

The present invention addresses the need to rapidly counteract the toxic effects of acetaminophen overdose. In one aspect, the present invention is a solid oral dosage form that comprises both acetaminophen and a glutathione replenishing agent. As used herein, "solid oral dosage form" means any orally ingestible form for drug administration having a solid component, including tablets, capsules, powders, sachets, and the like.

The solid oral dosage form could be in the form of a tablet. As used herein, "tablet" means a compressed or molded solid dosage form of any shape or size, and includes caplets. A variety of different tablet formulations could be used, including immediate release tablets, sustained release tablets, matrix tablets, multi-layer tablets, multi-layer matrix tablets, extended release tablets, delayed release tablets, or pulsed release tablets. These could having coatings such as enteric coatings, rate-controlling coatings, semi-permeable coatings, and the like. The term "tablet" also includes osmotic delivery systems.

In some embodiments, the tablet of the present invention comprises an inner core and an outer structure around the inner core. The inner core comprises a glutathione replenishing agent in any suitable amount, as further explained in more detail below. The inner core may further comprise one or more excipient ingredients.

The outer structure comprises acetaminophen in any suitable amount, as further explained in more detail below. The outer structure may be a single unitary structure or comprise multiple (two or more) substructures such as layers or compartments. The outer structure may further comprise one or more excipient ingredients.

In some embodiments, the outer structure comprises a shell that surrounds the inner core, wherein the acetaminophen is contained in the shell. Examples of such designs include tablet-in-tablet structures and core-in-cup structures. The shell may be a single unitary structure or comprise multiple (two or more) substructures such as layers or compartments.

The inner core may comprise an external barrier layer. As used herein, "barrier layer" means a layer that physically separates the portion(s) containing acetaminophen from the portion(s) containing the glutathione replenishing agent. The barrier layer is non-permeable to both acetaminophen and the glutathione replenishing agent. This barrier function may be achieved by appropriate implementation of design factors such as layer thickness, density, material composition, etc.

In some embodiments, the outer structure comprises a shell that surrounds the inner core and an external layer covering at least part of the shell. The external layer comprises an excipient ingredient. The acetaminophen could be contained in the shell, the external layer, or both.

In some embodiments, the pharmaceutical tablet is a multi-particulate tablet that comprises a bulk matrix and multiple particles held within the bulk matrix. The bulk matrix comprises acetaminophen in any suitable amount, as further explained in more detail below. The bulk matrix may be a homogenous mass, a heterogeneous mass, or may comprise multiple (two or more) substructures such as layers or compartments.

The particles comprise a glutathione replenishing agent. The particles may be granules, pellets, beads, grains, microcapsules, etc., and can have any shape or morphology. In some embodiments, the particles comprise a core granule comprising the glutathione replenishing agent and a barrier layer around the core granule. The total amount of the glutathione replenishing agent provided by the particles may be any suitable amount, as further explained in more detail below. The individual particles may have any suitable size depending on factors such as desired flow characteristic of the particles, content uniformity, and surface area. For example, the individual particles may have a size in the range of 100 µm to 2 mm.

The solid oral dosage form could be in the form of a pharmaceutical capsule. The pharmaceutical capsule comprises a degradable casing with acetaminophen and a glutathione replenishing agent contained therein. The acetaminophen is provided in one or more discrete units inside the casing. The glutathione replenishing agent is provided in one or more discrete units inside the casing, separately from the discrete unit(s) that contain acetaminophen.

In some cases, the capsule contains multiple discrete particles that comprise acetaminophen and other multiple discrete particles that comprise the glutathione replenishing agent. The particles may be granules, pellets, beads, grains, microcapsules, etc., and can have any shape or morphology. The individual particles may have any suitable size depending on factors such as desired flow characteristic of the particles, content uniformity, and surface area. The particles may have a size conventionally used in pharmaceutical capsules. For example, the individual particles may have a size in the range of 100 µm to 2 mm.

In another aspect, the invention is a method of treatment. The treatment may be for any condition that is conventionally treated with acetaminophen, such as pain or fever. The patient may be of any age category conventionally treated with acetaminophen, including infants, children, and adults. In some embodiments, the invention is a method of orally co-administering acetaminophen and a glutathione replenishing agent to the patient. The step of administering may be performed by the patients themselves or by another person (e.g. a caretaker, nurse, or clinician). In some embodiments, the method comprises administering a dosage form that simultaneously provides acetaminophen and a glutathione replenishing agent to the patient. In some embodiments, the invention is a method of treating a patient with acetaminophen while reducing hepatotoxicity associated with acetaminophen.

DETAILED DESCRIPTION

Figure 1A:
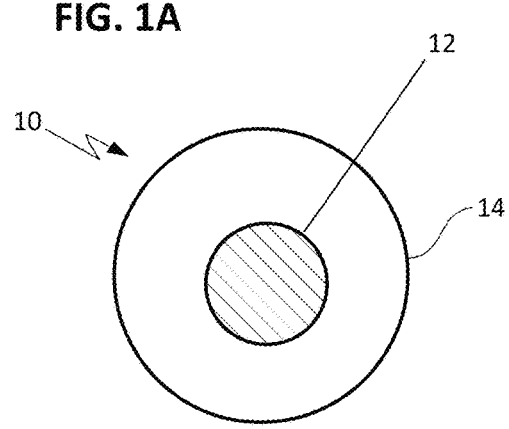
FIGS. 1A and 1B show an example of a tablet-in-tablet design.

This invention combines acetaminophen and a glutathione replenishing agent in a single solid oral dosage form. Co-administration of a glutathione replenishing agent in conjunction with acetaminophen would improve the safety of acetaminophen. In the case of acetaminophen overdose, the glutathione replenishing agent would rapidly counteract against the toxic effects. This type of product is often referred to in the industry as a "fixed dose combination" in which two or more drugs are contained in a single dosage form. The solid oral dosage form of the present invention combines acetaminophen and the glutathione replenishing agent in the manner described below.

1. Acetaminophen

The solid oral dosage form comprises acetaminophen. As used herein, the term "acetaminophen" also includes any pharmaceutically acceptable isomer, ester, polymorph, or salt thereof. The solid oral dosage form may contain any suitable amount of the acetaminophen to achieve therapeutic efficacy with administration in single or multiple units (e.g. the total effective dose could be divided in two tablets). In some embodiments, a single unit of the solid oral dosage form (e.g. a single tablet or single capsule) contains 100 mg to 1,500 mg of acetaminophen; in some cases, about 325 mg (i.e. ±5%); in some cases, about 500 mg (i.e. ±5%); and in some cases, about 650 mg (i.e. ±5%).

2. Glutathione Replenishing Agent (Antidote)

The solid oral dosage form further comprises a glutathione replenishing agent that promotes glutathione production to negate the adverse hepatic effects of acetaminophen. As used herein, a particular glutathione replenishing agent identified herein also includes any pharmaceutically acceptable isomer, ester, polymorph, or salt thereof. The glutathione replenishing agent acts as an antidote by replenishing the supply of glutathione that works to detoxify NAPQI. Examples of antidotes that could be used include N-acetylcysteine (NAC), glutathione, methionine, cysteine, cysteamine, and dimercaprol. Of these, N-acetylcysteine is the most widely used for first-line treatment.

The amount of the glutathione replenishing agent contained in each single unit of the solid oral dosage form could depend on various factors, such as the desired size of the dosage form, minimizing side effects, efficacy in different overdose scenarios, etc. In some embodiments, a single unit of the solid oral dosage form contains at least 50 mg of the glutathione replenishing agent (e.g. NAC). In some embodiments, a single unit of the solid oral dosage form contains 50-800 mg of the glutathione replenishing agent (e.g. NAC).

It is not necessary that a single unit of the solid oral dosage form must contain a therapeutically effective amount of the glutathione replenishing agent. In a typical overdose situation, the subject ingests many doses of the acetaminophen, far in excess of the maximum recommended daily dosage, whether accidentally or intentionally. For example, in a suicide attempt, the subject may ingest the entire contents of a 100 count bottle. As such, a large amount of the glutathione replenishing agent may not be necessary for each single unit of the solid oral dosage form. Also, having lower amounts of the glutathione replenishing agent would reduce any side effects that might result.

In some embodiments, in a single unit of the solid oral dosage form, the ratio (by weight) of the glutathione replenishing agent (e.g. NAC) to the acetaminophen is in the range of 1:25 (for example, 20 mg of NAC and 500 mg of acetaminophen) to 1:1 (for example, 325 mg of NAC and 325 mg of acetaminophen); and in some cases, in the range of 1:20 to 1:5. In some embodiments, in a single unit of the solid oral dosage form, the amount of the glutathione replenishing agent (e.g. NAC) is less than 160 mg; in some cases, less than 120 mg; and in some cases, less than 80 mg.

3. Tablet Formulation

In some embodiments, the solid oral dosage form is in the form of a tablet. As used herein, "tablet" means a compressed or molded solid dosage form of any shape or size. Examples of tablet shapes include round, square, oval, modified oval, elliptical, cylindrical (e.g. caplets), etc. A monolithic tablet made of a homogenous mixture of acetaminophen and the glutathione replenishing agent is easy to manufacture and could be the first choice approach. However, making the combination product in such a manner would present several problems.

One major problem is that NAC has an unpleasant smell and taste because of the sulfhydryl group. Other sulfur-containing glutathione replenishing agents may also have an unpleasant smell and taste. Another major problem is that glutathione replenishing agents may be chemically incompatible with acetaminophen. In particular, the acidic carboxyl groups on NAC and glutathione may cause acid hydrolysis of the amide group on acetaminophen. Thus, it may be beneficial to physically separate the acetaminophen from the glutathione replenishing agent within the solid dosage form.

The present invention contemplates a tablet formulation that mitigates one or both of the above-mentioned problems. The tablet formulation may be designed to keep the acetaminophen physically separate from the glutathione replenishing agent. Also, the tablet formulation may be designed to mask the smell/taste of the glutathione replenishing agent to make it more palatable. This invention contemplates a variety of tablet designs to achieve one or both of these objectives, as explained below.

3(a). Tablet Core Design

Figure 1B:
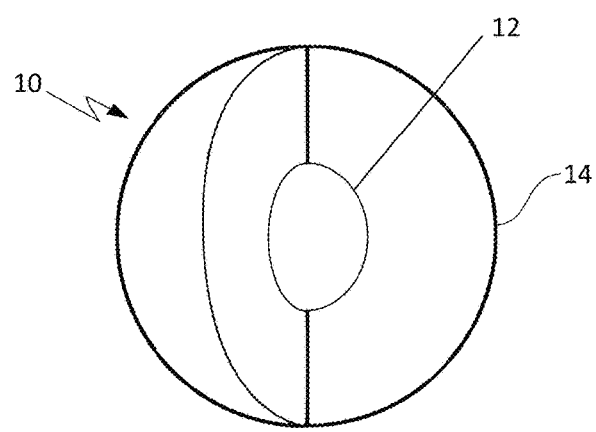

The tablet dosage form could be constructed with a tablet core that contains the glutathione replenishing agent. A variety of different types of such tablet core structures are possible, including tablet-in-tablet and core-in-cup architectures. FIG. 1A (cross-section view) and FIG. 1B (cut-away view) show an example of a tablet-in-tablet design. In this example, tablet 10 has an inner core 12 containing the glutathione replenishing agent. The inner core 12 is encapsulated within an outer shell 14 containing acetaminophen. Inner core 12 and outer shell 14 may further contain excipient ingredients to improve the tablet's physical or chemical properties (e.g. stability, hardness, friability, disintegration, dissolution, content uniformity, tablet size, etc.)

An example of a tablet-in-tablet construction is described in U.S. Patent Application Publication No. 2008/0175908 (Liu et al). Here, an inner core of conjugated estrogen was made by wet granulation and then compressed into tablet form. Separately, a dry blend of medroxyprogesterone acetate with excipient ingredients was made. This dry blend was then compressed onto the preformed estrogen core using an 11 mm round convex tooling on a Kilian RUD compression machine to create an outer shell around the estrogen inner core. This resulted in a finished tablet with the estrogen core surrounded by a shell of medroxyprogesterone.

Another example of a tablet-in-tablet construction is described in U.S. Pat. No. 9,572,780 (Lim et al). In this example, an inner core of metformin hydrochloride was made to provide prolonged release of the drug. This inner core was sprayed with a film of hydroxypropyl methyl cellulose as a barrier layer. The outer shell for the tablet was made by spraying a suspension of glimepiride onto the barrier-coated inner core.

Figure 2:
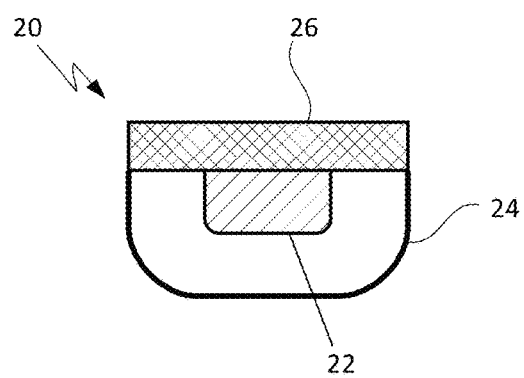
FIG. 2 shows an example of a core-in-cup tablet design.

FIG. 2 is a cross-section view showing an example of a core-in-cup tablet design. Tablet 20 has a shell that comprises a cup 24 made of acetaminophen and suitable excipient ingredient(s) to form a sturdy cup-like structure. The inner core 22 contains a glutathione replenishing agent, and optionally, suitable excipient ingredient(s). The inner core 22 is contained within the cup 24. The shell further comprises a capping layer 26 made of suitable excipient ingredient(s) that covers over cup 24 and the inner core 22 to hold the structure together. Alternatively, the acetaminophen could be contained in the capping layer 26 instead of the cup 24 structure. In yet another alternative, acetaminophen could be contained in both the cup 24 and the capping layer 26.

One particular core-in-cup design is described in Sokara et al, "Pulsatile core-in-cup valsartan tablet formulations: In vitro evaluation" (2013 August) *Asian Journal of Pharmaceutical Sciences*, vol. 8(4):234-243. The inner core of the tablets were made with valsartan and various excipient ingredients using a single punch tablet press machine, equipped with 6 mm flat-faced punches. The "cup" was made by filling a punch die with ethyl cellulose powder and making a flat, compacted powder bed. The preformed inner core was placed in the center of the powder bed, and then the gap between the core and the punch die was filled manually with more ethyl cellulose powder so that the inner core was fully covered. A polymer plug was added onto the top. The tablet was compressed to produce the desired core-in-cup configuration. A second layer containing additional valsartan was added to the bottom by compressing the core-in-cup structure onto a powder blend layer, resulting in a bilayer core-in-cup tablet.

Figure 3:
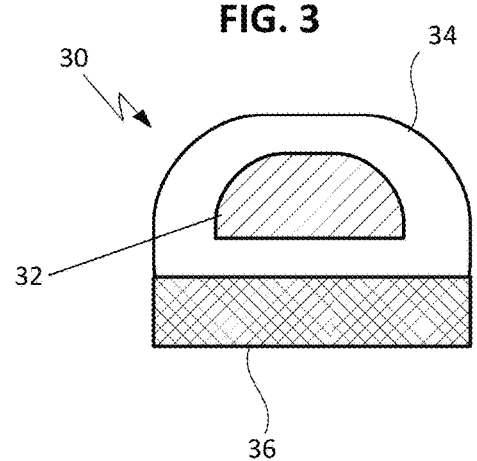
FIG. 3 shows another possible tablet core design.

FIG. 3 is a cross-section view showing another possible tablet core design. In this example, the tablet 30 is constructed with an inner core 32 containing the glutathione replenishing agent. Tablet 30 has an outer structure that comprises a shell 34 of excipient material(s) that surrounds and firmly encases inner core 32. The outer structure further comprises a bottom layer 36, which contains acetaminophen and is pressed onto the structure to form the final bilayer tablet 30.

Figure 4:
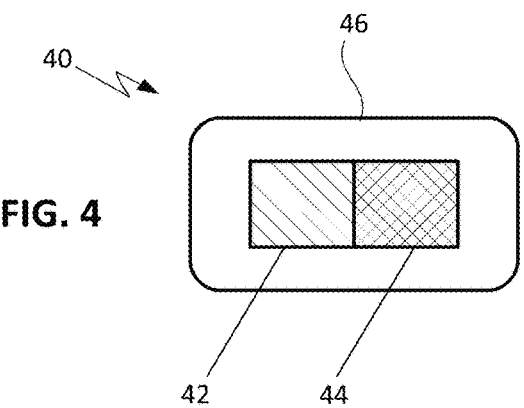
FIG. 4 shows another possible tablet design in which the tablet core has a multi-compartment structure.

FIG. 4 is a cross-section view showing another possible tablet design in which the tablet core has a multi-compartment structure. In this example, there is a first inner core 42 containing acetaminophen and a second inner core 44 containing the glutathione replenishing agent. The two cores could be separated by a physical barrier to protect against chemical interaction with each other. The inner cores 42 and 44 are surrounded by a shell 46 of excipient material(s) to firmly encase inner cores 42 and 44.

3(b). Multi-Particulate Tablet Design

Figure 5A:
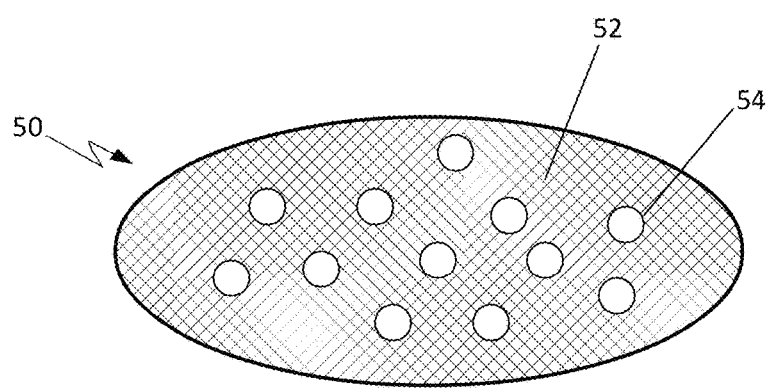
FIGS. 5A and 5B show an example of a multi-particulate tablet.
Figure 5B:
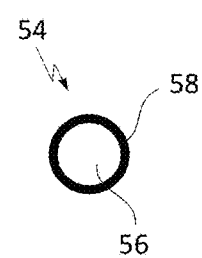

The tablet dosage form could be constructed with multiple discrete particles embedded within the tablet matrix. As an example, FIGS. 5A and 5B show a multi-particulate tablet 50. As shown in FIG. 5A (cross-section view), the tablet 50 contains multiple pellets 54 embedded within the tablet bulk matrix 52. The acetaminophen is contained within the bulk matrix 52. The pellets 54 contain the glutathione replenishing agent and are coated with a barrier film 58 to protect against chemical interaction with the acetaminophen in the bulk matrix.

An example of this type of tablet construction is described in Burke et al, "Stability Enhancement of Drug Layered Pellets in a Fixed Dose Combination Tablet" (2013) *AAPS PharmSciTech*. 14(1):312-320. In this example, denagliptin pellets were made by spray coating microcrystalline cellulose beads with the denagliptin drug, and then adding a sealant coating of hypromellose. The denagliptin pellets were then mixed with metformin and the resulting blend was compressed into tablets. Another example of a multi-particulate tablet formulation is described in U.S. Pat. No. 7,438,929 (Beckert et al).

3(c). Tablet Manufacturing

The tablets of the present invention could be made by any suitable manufacturing process. Typical processes for manufacturing tablets include wet granulation, dry granulation, direct compression, or combinations thereof. Manufacturing techniques for making tablet designs of the present invention are known in the art, such as the techniques described in U.S. Pat. No. 9,415,016 (Friedl et al), U.S. Pat. No. 8,685,451 (Toneguzzo et al), U.S. Pat. No. 9,597,338 (Berner et al), and U.S. Pat. No. 3,558,768 (Klippel).

Excipient ingredients could be used in any of the various parts of the tablet. As used herein, the term "excipient" means a substance, not itself an active therapeutic agent, that is used as a carrier or vehicle for delivery of the therapeutic agent or added to a pharmaceutical composition to improve its handling, storage, disintegration, dispersion, dissolution, release, or to facilitate formation of a dose unit of the composition into a discrete article such as a capsule or tablet suitable for oral administration. Examples of excipient ingredients include such materials as binders (such as sucrose, lactose, starch, microcrystalline cellulose, hydroxypropyl cellulose, and synthetic polymers such as polyvinylpyrrolidone or polyethylene glycol, etc.); disintegrants such as sodium starch glycolate, croscarmellose sodium, or crospovidone; and lubricants such as talc, silica, or magnesium stearate. Other examples of excipient materials include glidants (e.g. colloidal silicon dioxide), flavorants (e.g. menthol, peppermint, mint flavors, fruit flavors, chocolate, vanilla, bubblegum flavors, coffee flavors, etc.), preservatives (e.g. citric acid, sodium citrate, vitamin A, vitamin E, vitamin C), and diluents.

4. Capsule Formulation

In some embodiments, the solid oral dosage form is in the form of a capsule. Capsules are solid dosage forms in which the drug substance is enclosed in a degradable casing. Like the tablet design described above, the capsule could be designed to physically separate the acetaminophen from the glutathione replenishing agent and/or mask the taste or smell of the glutathione replenishing agent. Excipient ingredients, as described above, could be used in any of the various parts of the capsule formulation.

4(a). Multi-Particulate Capsule

Figure 6A:
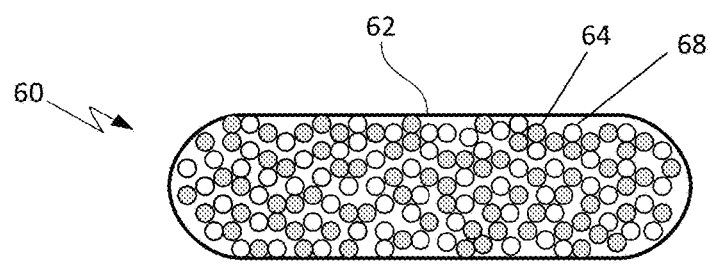
FIGS. 6A and 6B show an example of a multi-particulate capsule.
Figure 6B:
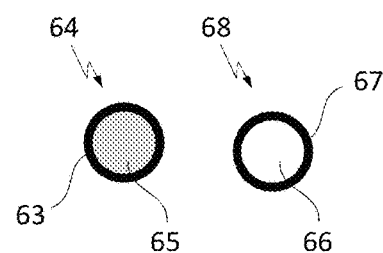

The capsule dosage form could be designed as a capsule containing multiple discrete drug particles. A variety of different types of particles could be used, including granules, pellets, beads, grains, microcapsules, etc., and can have any shape or morphology. As an example, FIGS. 6A and 6B show a multi-particulate capsule 60. As shown in FIG. 6A (cross-section view), the capsule 60 has a degradable casing 62, which is filled with drug granules 64 and 68. FIG. 6B shows a close-up view of the granules 64 and 68. Granules 64 comprise an inner mass 65 containing acetaminophen and a protective coating 63. Granules 68 comprise an inner mass 66 containing the glutathione replenishing agent and a protective coating 67.

4(b). Mini-Tablets in Capsules

Figure 7:
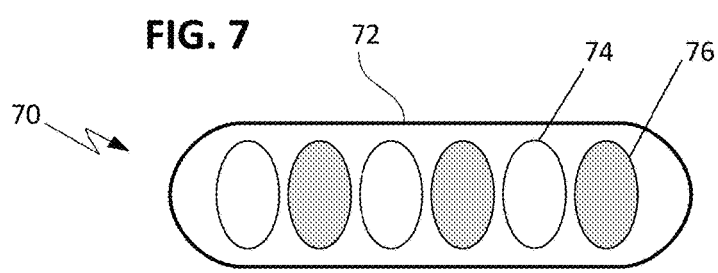
FIG. 7 shows an example of a mini-tablet capsule.

The capsule dosage form could be a capsule containing multiple mini-tablets. As an example, FIG. 7 shows a mini-tablet capsule 70. This cross-section view of the capsule 70 shows a capsule casing 72, which is filled with several mini-tablets 74 and 76. Mini-tablets 74 contain acetaminophen and have a protective coating. Mini-tablets 76 contain the glutathione replenishing agent and have a protective coating. Additional examples are given in Reza Fassihi, "Modified-Release Delivery Systems: Extended-Release Capsule Platform" in *Pharmaceutical Dosage Forms: Capsules* (ed. Augsburger) CRC Press (2017).

5. Treatment Method & Dosing

The pharmaceutical composition of this invention could allow the administration of acetaminophen with improved safety. The patient receives a dosage form that simultaneously provides acetaminophen and a glutathione replenishing agent. In some embodiments, the method comprises administering a solid oral dosage form of the present invention. The solid oral dosage form may be dosed in any suitable manner conventional in the use of acetaminophen. The patient may receive regular intermittent dosing, for example, with a dosing frequency of every 4 to 6 hours or every 4 to 8 hours. In some embodiments, a first dose is administered and then a second dose is administered within a time that is 3.5 to 8.5 hours after the first dose, for example, within 4 to 6 hours after the first dose. The maximum single dose of acetaminophen administered may be less than 1,250 mg (e.g. maximum one-time dose of 1,000 mg). The maximum amount of acetaminophen administered over a 24 hour period may be less than 5 grams (e.g. maximum total amount of 4 grams over a 24 hour period).

In the oral dosage form, the acetaminophen is compartmentally separated from the glutathione replenishing agent. As a result, it is possible that there is no significant chemical interaction between the acetaminophen and glutathione replenishing agent. In some cases, the glutathione replenishing agent is contained within multiple small discrete subunits. Each discrete subunit may have a barrier layer to provide separation from acetaminophen. In some cases, the glutathione replenishing agent is contained within a single subunit of the dosage form, such as a core. The subunit may be separated from the acetaminophen by a barrier layer.

The glutathione replenishing agent may be excluded from the external surface of the dosage form. This means that the glutathione replenishing agent could be isolated from the external surface by any suitable design of the dosage form, such as use of coating layers, embedding within a matrix, encapsulation within other materials, etc. The acetaminophen may or may not be exposed to the external surface of the dosage form. In some embodiments, the glutathione replenishing agent may be excluded from the external surface of the dosage form whereas the acetaminophen is exposed on the external surface of the dosage form.

In some embodiments, the amount of glutathione replenishing agent received by the patient for each dose is less than 160 mg; in some cases, less than 120 mg; and in some cases, less than 80 mg. In some embodiments, the amount of glutathione replenishing agent (e.g. NAC) relative to the acetaminophen (ratio by weight) received by the patient is in the range of 1:25 to 1:1; and in some cases, in the range of 1:20 to 1:5.

Peak drug levels for oral acetaminophen occurs rapidly, for example, within 30 to 60 minutes depending on the particular formulation. However, hepatic toxicity may occur much later, for example, three to five days after ingestion of a toxic dose. As such, in some embodiments, the peak drug level for the glutathione replenishing agent occurs after the peak drug level for acetaminophen as measured in blood, serum, or plasma after ingestion of the dose combination.

6. Experimental Work

Four different experimental tablet formulations of acetaminophen (APAP) and/or N-acetylcysteine (NAC) were made. The excipient was a mixture of microcrystalline cellulose, magnesium stearate, silica dioxide, and dicalcium phosphate. The compositions of experimental tablets #1-4 are given below. Odor and taste testing was performed by two observers. The observers were blinded when presented for odor and taste perception by blind codes attached to labels on the sample containers holding the experimental tablets. The results of the odor and taste testing are shown in Table 1 below.

Figure 8A:
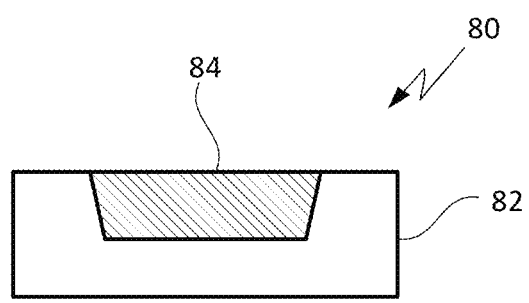
FIGS. 8A and 8B are schematic diagrams showing the structure of an experimentally made tablet.
Figure 8B:
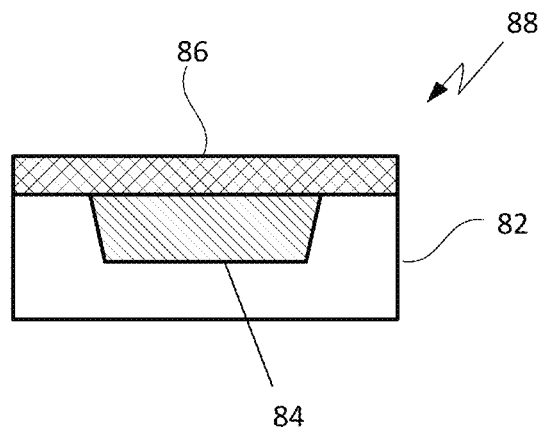

FIGS. 8A and 8B are schematic diagrams showing the structure of tablet #4. As shown in FIG. 8A, a first stage tablet 80 was made by pressing an APAP mixture 82 made of 100 mg of APAP plus excipient. Next, a small pocket was dug into the tablet to form a pocket. This pocket was filled with an NAC mixture 84 made of 75 mg of NAC plus excipient. The tablet 80 was then pressed again. As shown in FIG. 8B, the top of the tablet was then covered with a layer 86 of carnauba wax to serve as a barrier. The resulting tablet 88 is a schematic representation of experimental tablet #4, which was about 8 mm wide in diameter and about 2.5 mm deep in thickness.

Tablet #1: NAC+excipient pressed into tablet.
Tablet #2: APAP+excipient pressed into tablet.
Tablet #3: APAP+excipient in a "cup" with NAC+excipient in a "core" without a barrier.
Tablet #4: APAP+excipient in a "cup" with NAC+excipient in a "core" covered with a carnauba wax barrier.

TABLE 1

|  | Tablet #1 | Tablet #2 | Tablet #3 | Tablet #4 |
|---|---|---|---|---|
| NAC amount (mg) | 95 | zero | 75 | 75 |
| Observer #1, odor test | (+) sulfur odor | (−) no sulfur odor | (+) sulfur odor | (−) no sulfur odor |
| Observer #1 taste test | (+) harsh taste | (−) no harsh taste | (+) harsh taste | (−) faint taste* |
| Observer #2, odor test | (+) sulfur odor | (−) no sulfur odor | (+) sulfur odor | (−) no sulfur odor |
| Observer #2, taste test | (+) harsh taste | (−) no harsh taste | (+) harsh taste | (−) faint taste† |

*Faint harsh taste after 1-2 seconds held on tongue.
†Faint harsh taste after after swallowing.

7. Conclusion

The foregoing description and examples have been set forth merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A pharmaceutical tablet comprising:
    an inner core comprising N-acetylcysteine in an amount of at least 50 mg; and
    a shell that surrounds the inner core, the shell comprising acetaminophen in an amount of 100 to 1,500 mg;
    wherein the shell comprises a cup structure surrounding a portion of the inner core and a capping layer over the cup structure, and wherein the acetaminophen is contained in the cup structure, the capping layer, or both; and
    wherein the ratio (by weight) of N-acetylcysteine to the acetaminophen is in the range of 1:20 to 1:5.

2. The pharmaceutical tablet of claim 1, wherein the outer structure comprises a shell that surrounds the inner core and an external layer covering at least part of the shell, wherein the external layer comprises an excipient ingredient, and wherein the acetaminophen is contained in the shell, the external layer, or both.

3. The pharmaceutical tablet of claim 1, wherein the inner core comprises an external barrier layer.

4. The pharmaceutical tablet of claim 1, wherein the amount of N-acetylcysteine is at least 50 mg and less than 160 mg.

5. The pharmaceutical tablet of claim 1, wherein the amount of N-acetylcysteine is 50 to 800 mg.

6. The pharmaceutical tablet of claim 3, wherein the external barrier layer is non-permeable to both acetaminophen and N-acetylcysteine.

7. The pharmaceutical tablet of claim 1, wherein the amount of acetaminophen in the shell is about 325 mg, or about 500 mg, or about 650 mg.

8. The pharmaceutical tablet of claim 7, wherein the amount of N-acetylcysteine is at least 50 mg and less than 160 mg.

9. The pharmaceutical tablet of claim 7, wherein the amount of N-acetylcysteine is at least 50 mg and less than 120 mg.

10. The pharmaceutical tablet of claim 7, wherein the amount of acetaminophen in the shell is about 325 mg.

11. The pharmaceutical tablet of claim 7, wherein the amount of acetaminophen in the shell is about 500 mg.

12. The pharmaceutical tablet of claim 7, wherein the amount of acetaminophen in the shell is about 650 mg.

* * * * *